United States Patent

Bergthaller et al.

Patent Number: 4,870,000
Date of Patent: Sep. 26, 1989

[54] COLOR PHOTOGRAHIC RECORDING MATERIAL CONTAINING A COUPLER WHICH RELEASES A PHOTOGRAPHICALLY ACTIVE COMPOUND

[75] Inventors: Peter Bergthaller, Bergisch Gladbach; Rudolf Stolzenburg, Langenfeld; Dirk Hübner, Cologne, all of Fed. Rep. of Germany

[73] Assignee: Agfa-Gevaert Aktiengesellschaft, Leverkusen, Fed. Rep. of Germany

[21] Appl. No.: 170,915

[22] Filed: Mar. 21, 1988

[30] Foreign Application Priority Data

Apr. 4, 1987 [DE] Fed. Rep. of Germany ....... 3711418

[51] Int. Cl.$^4$ .................. G03C 1/34; G03C 1/06
[52] U.S. Cl. .................. 430/505; 430/506; 430/544; 430/556; 430/557; 430/558; 430/955; 430/957
[58] Field of Search ............ 430/505, 544, 558, 957, 430/556, 557

[56] References Cited

U.S. PATENT DOCUMENTS

| | | | |
|---|---|---|---|
| 3,841,880 | 10/1974 | Kertel | 430/505 |
| 4,259,437 | 3/1981 | Webb | 430/382 |
| 4,410,618 | 10/1983 | Vanmeter et al. | 430/219 |
| 4,518,685 | 5/1985 | Yagihara et al. | 430/505 |
| 4,591,548 | 5/1986 | Delprato | 430/389 |
| 4,690,885 | 9/1987 | Yagihara et al. | 430/212 |

Primary Examiner—Paul R. Michl
Assistant Examiner—Mark R. Buscher
Attorney, Agent, or Firm—Connolly & Hutz

[57] ABSTRACT

A color photographic recording material containing a coupler which releases a photographically active compound.

Couplers corresponding to formula (I) couple with color developers to form yellow to yellow-orange dyes and, in doing so, release the residue X as a photographically active compounds. Where X is a development inhibitor, remarkably high inter-image and edge effects can be obtained.

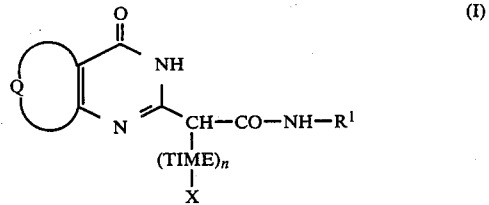

in which
R$^1$ represents alkyl, a heterocyclic or carbocyclic aromatic group or -NH-CO-R$^2$;
R$^2$ represents alkyl, aryl or -NH-R$^3$;
R$^3$ represents alkyl or aryl;
Q represents the groups to complete a fused, optionally substituted benzene or heterocyclic ring;
X represents the residue of a photographically active compound;
TIME represents a bond which, on reaction of the coupler with the oxidation product of a color developer, is released together with the residue X attached thereto and, in turn, releases the residue X as a photographically active compound under the development conditions;
n=0 or 1.

7 Claims, No Drawings

COLOR PHOTOGRAHIC RECORDING MATERIAL CONTAINING A COUPLER WHICH RELEASES A PHOTOGRAPHICALLY ACTIVE COMPOUND

This invention relates to a color photographic recording material comprising at least one photosensitive silver halide emulsion layer containing a coupler which releases a photographically active group, for example a development inhibitor, on color development.

It is known that chromogenic development may be carried out in the present of compounds which, on development, release substances which are capable of imagewise diffusion and which develop a certain effect, for example are capable of influencing the development of silver halide. If the result of this effect is that further development is inhibited, the compounds in question are call DIR compounds (DIR=development inhibitor releasing). The DIR compounds may be compounds which react with the oxidation product of a color developer with elimination of an inhibitor group to form a dye (DIR couplers) of compound which release the inhibitor without forming a dye in the process. Such compounds are also called DIR compounds in the narrower sense.

DIR couplers are known, for example, from US-A-3 148 062, US-A-3 227 554, US-A-3 615 506, US-A-3 617 291 and DE-A-2 414 006.

However, the diffusible, photographically active compounds which are released during development may also be, for example, a dye, a coupler, a hardener, a silver halide solvent, a fogging agent, a development accelerator, a developer compound, a bleach inhibitor, a beach accelerator, a mordant or a sensitizer.

The development inhibitors released are generally heterocyclic mercapto compounds to derivatives of benzotriazole. With regard to the DIR compounds which couple in substantially colorless form, reference is made, for example, to US-A-3 632 345, DE-A-23 59 295 and DE-A-25 40 959. A number of photographic effects which influence image quality can be obtained by using DIR compounds. Such effects include, for example, the reduction of gradation, the production of a finer color grain, the improvement of sharpness through the so-called edge effect and the improvement of color purity and color brilliance through so-called inter-image effects. In this connection, reference is made, for example, to the Article by C. R. Barr, J. R. Thirtle and P. W. Vittum entitled "Development-Inhibitor-Releasing (DIR) Couplers in Color Photography" in Photographic Science and Engineering 13, 74 (1969).

DIR compounds which couple without dye formation have the advantage over DIR couplers which couple with dye formation that they may be universally used so that the same compound may be used in all photosensitive layers of a color photographic recording material irrespective of the color to be produced. By contrast, DIR couplers can generally be used in only some of the photosensitive layers on account of the color produced from them, unless the secondary color density attributable to them is tolerable in the other layers. This advantage of the DIR compounds is offset by the disadvantage that they are generally less reactive than the DIR couplers. In practice, therefore, it is customary to use DIR couplers, if neccessary two or more different DIR couplers in the same recording material, different DIR couplers having to be associated with the differently spectrally sensitized layers according to the color produced from the DIR couplers.

Normally, it is important that the photographically active compound be rapidly released from the coupler during development, particularly when the photographically active compound is intended to influence the further course of development. It is thus very desirable for the couplers in question to be highly active. In this connection, particular significance is attributed to the group of the photographically active compound which is attached to the coupling position of the coupler, the so-called leaving group.

The object of the present invention is to provide a color photographic recording material which contains couplers from which a residue attached to the coupling position is released as a photographically active compound during development.

The present invention relates to a color photographic recording material comprising at least one photosensitive silver halide emulsion layer and, associated therewith, a coupler which is capable of releasing a photographically active compound, characterized in that the coupler corresponds to the following formula (I)

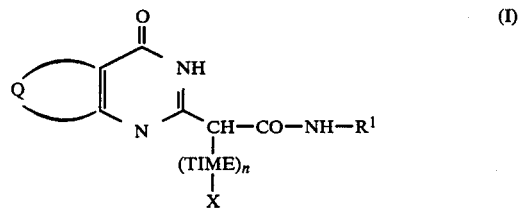

in which
- $R^1$ represents alkyl, a heterocyclic or carbocyclic aromatic group or —NH—CO—$R^2$;
- $R^2$ represents alkyl, aryl or —NH—$R^3$;
- $R^3$ represents alkyl or aryl;
- Q represents the residue required to complete a fused, optionally substituted benzene or heterocyclic ring;
- X represents the residue of a photographically active compound;
- TIME represents a bond which, on reaction of the coupler with the oxidation product of a color developer, is released together with the residue X attached thereto and, in turn, releases the residue X as a photographically active compound under the development conditions; n=0 or 1.

An alkyl radical represented by $R^1$, $R^2$ or $R^3$ in formula I is linear or branched, substitiuted or unsubstituted and contains 1 to 20 carbons atoms; examples are methyl, ethyl, butyl, hexyl, dodecyl.

An aromatic group represented by $R^1$ in formula I may be an aryl group, for example phenyl, or a heterocyclic group, for example thiazole, benzothiazole, thienyl or pyridyl.

The groups mentioned may be substituted, for example by alkyl, alkoxy, halogen, alkoxycarbonyl, carbamoyl, sulfamoyl or acylamino, the acyl radical being derived from aliphatic or aromatic carboxylic acids or sulfonic acids or from carbamic acids or carbonic acid monoesters. $R^1$ preferably represents phenyl which is substituted by a group imparting resistance to diffusion, for example in the form of an alkoxy, alkoxycarbonyl, carbamoyl, sulfamoyl, sulfonamido or carbonamido group containing 8 or more carbon atoms. However, a radical which imparts resistance to diffusion may also be present as a substituent on the ring completed by Q or may be omitted altogether. A heterocyclic ring completed by Q is, for example, a thiophene, pyridine, thiazole, furan, pyrazole, benzofuran or thionaphthene ring.

A bond represented by TIME in formula I is a group which, after release from the coupling position of the coupler during its coupling with the oxidation product of the silver halide developer, is capable of releasing a photographically active group attached thereto, in the present case a triazole corresponding to formula II, in a subsequent reaction. The group TIME is also called a tming group because, where such a group is present, the photographically active group attached thereto is often released and can become active with delay. Known timing groups are, for example, a group

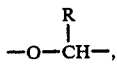

where the O atom is attached to the coupling position of the coupler while the C atom is attached to an N-atom of a photographically active compound (for example DE-A-27 03 145), a group which, after release from the coupler, undergoes an intramolecular nucleophilic displacement reaction and, in the process, releases the photographically active compound (for example DE-A-28 55 697), a group in which, after release from the coupler, electron transfer can take place along a conjugated system so that the photographically active compound is released (for example DE-A-31 05 026) or a group

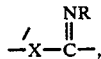

in which X (for example —O—) is attached to the coupling position of the coupler while the C atom is attached to an atom of the photographically active compound and in which R is an aryl radical for example (for example EP-A-0 127 063). The group TIME may also be a group which, after elimination from the coupling position of the coupler, can itself enter into a coupling reaction or a redox reaction and, in consequence of that reaction, releases the group X attached to it.

The releasable group X is, for example, a halogen atom (for example F, Cl, Br, I) or an organic group which, in general, is attached to the coupling position of the coupler molecule by an oxygen, sulfur or nitrogen atom (optionally via a group TIME). If the releasable group is a cyclic group, it may be attached to the coupling position of the coupler molecule (or to the group TIME either directly by an atom which is part of a ring, for example a nitrogen atom, or indirectly via an intermediate bond. Releasable groups such as these are known in large numbers, for example as leaving groups of 2-equivalent yellow couplers.

Examples of releasable groups attached via oxygen correspond to the following formula

in which $R^4$ is an acyclic or cyclic organic radical, for example alkyl, aryl, a heterocyclic group or acyl, which is derived for example from an organic carboxylic or sulfonic acid. In particularly preferred releasable groups of this type, $R^4$ is an optionally substituted phenyl group. Groups such as these are described, for example, in US-A-3 408 194, DE-A-24 56 076.

Examples of releasable groups attached via nitrogen can be found in the following German Offenlegungsschrifts (DE-A-):
2057941, 2163 812, 2213461, 22 19 917, 22 61 361, 2263875, 2318 807, 23 29 587, 23 44 155, 23 63 675, 2433812, 2441 779, 24 42 703, 25 28 638, 25 28 860, 2637817, 2828 373, 30 20 416.

The rings in question are all 5-or 6-membered heterocyclic rings which are attached to the coupling position of the coupler by a ring nitrogen atom. The heterocyclic rings often contain activating groups, for example carbonyl or sulfonyl groups or double bonds, adjacent the nitrogen atom which establishes the bond to the coupler molecule.

Where the releasable group is attached to the coupling position of the coupler by a sulfur atom, it may be the residue of a diffusible mercapto compound which is capable of inhibiting the development of silver halide. Inhibitor residues such as these have often been described as releasable groups attached to the coupling position or couplers, including open-chain ketomethylene couplers (for example in US-A-3 227 554).

The releasable group X is preferably the residue of a photographically active compound which is attached to the coupling position of the coupler or to the timing group TIME by a nitrogen atom of a 1,2,3-or 1,2,4-triazole ring. A group X such as this corresponds for example to the following formula

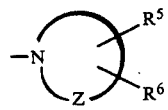

in which
Z represents the balance required to complete a 1,2,3- or 1,2,4-triazole ring;
$R^5$ and $R^6$ represent H, alkyl, aryl, a heterocyclic group, alkoxy, —S—$R^7$, amino, acylamino, a carboxylic ester group or —CO—$NR^8R^9$, or
$R^5$ and $R^6$ together represent (if the ring completed by Z is a 1,2,3-triazole ring) the groups required to complete a fused, optionally substituted, preferably aromatic ring, for example a tetrahydrobenzene ring, a benzene ring or a thiophene ring, with the proviso that at least one of the radicals
$R^5$ and $R^6$ represents a photographically active group or the compound

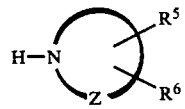

(II)

as a whole is a photographically active compound after release;
$R^7$ represents alkyl, cycloalkyl, aralkyl, alkenyl, alkynyl or aryl;
$R^8$ represents alkyl, aralkyl or aryl;
$R^9$ represents H or has the same meaning as $R^8$ or $R^8$ and $R^9$ together represent the balance required to complete a cyclic amino group.

An alkyl radical represented by $R^5$, $R^6$, $R^7$, $R^8$ or $R^9$ in formula II may be linear or branched and may contain up to 10 carbon atoms; examples are methyl, ethyl, propyl, isopropyl, butyl, s-butyl, t-butyl, pentyl, hexyl, octyl. The alkyl radicals may be substituted, for example by hydroxyl, alkoxy, alkylthio, acylamino or acyclic imide groups.

A cycloalkyl radical represented by $R^7$ is for example cyclohexyl, an aralkyl radical ($R^7$, $R^8$) is for example benzyl; an alkenyl radical is for example allyl or 2-butenyl; an alkynyl radical is for example propynyl.

A cyclic amino group ($R^8$, $R^9$) is for example a piperidino or morpholino group.

A cyclic imido group is for example a succinimido group, a maleic imido group, a phthalimido group, a hexahydrophthalimido group or a group corresponding to the following formula

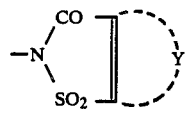

in which Y is the balance required to complete a carbocyclic or heterocyclic, optionally substituted ring.

A heterocyclic group represented by $R^5$ or $R^6$ is, for example, a furyl, thiazolyl or 1,2,4-triazolyl group. A heterocyclic group such as this may contain further substituents, for example alkyl, alkoxy, alkylthio (—S—$R^7$).

The advantageous properties of the couplers according to the invention are presumably attributable to the fact that the triazole ring not only would appear to be a good leaving group, so that the couplers are highly reactive, but would also appear to show a certain tendency to be adsorbed to the silver halide grain, thus influencing the processes taking place during the development of the silver halide. The groups determining the activity of the photographically active compound would appear to come into particularly good contact with the surface of the silver halide grain. According to the invention, therefore, the photographically active compound is preferably a compound which influences the development of the silver halide, for example a development accelerator, a fogging agent, a bleach accelerator or, more preferably, a development inhibitor. Where the photographically active compound is a development inhibitor, at least one of the radicals $R^5$ and $R^6$ is preferably —S—$R^7$, $C_2$-$C_{10}$ alkoxycarboxyl or a heterocyclic group.

The couplers according to the invention give yellow to yellow-reddish dyes by coupling with developer oxidation products during chromogenic development. Their main significance lies in the fact that they release the particular photographically active compound imagewise during the development process. Because they are highly active, they may be used in comparatively low concentrations. This enables them to be used even in those layers of the color photographic recording material in which magenta or cyan dyes are principally produced without the particular dye image being significantly affected by a yellow secondary density.

The following are examples of particularly useful DIR couplers for the purposes of the invention:

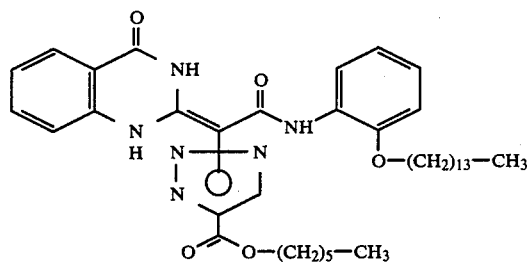

D-1

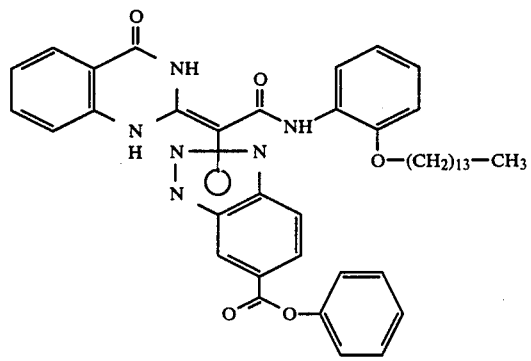

D-2

-continued
D-3
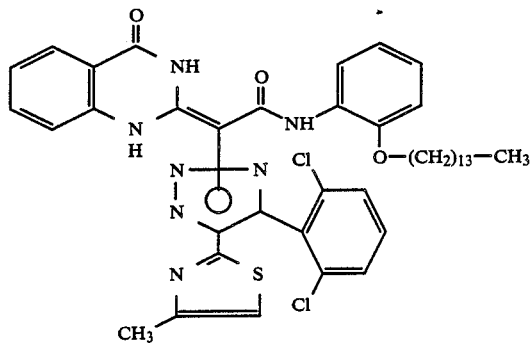
D-4
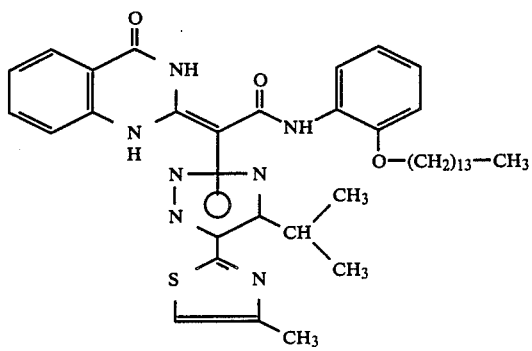
D-5
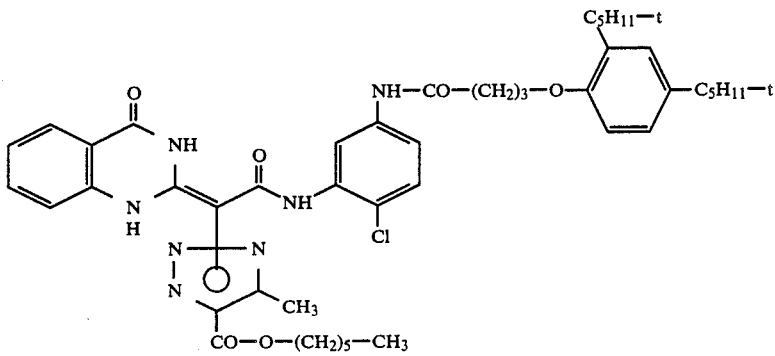
D-6
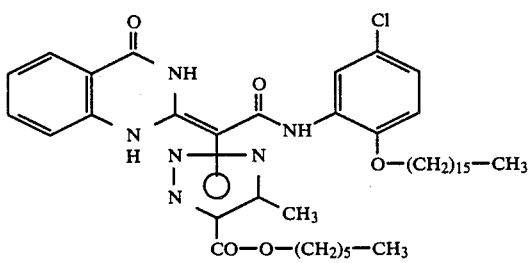
D-7
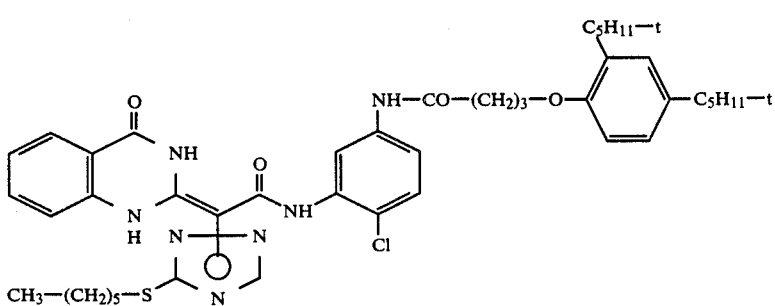

D-8
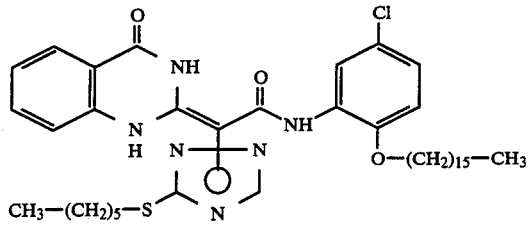
D-9
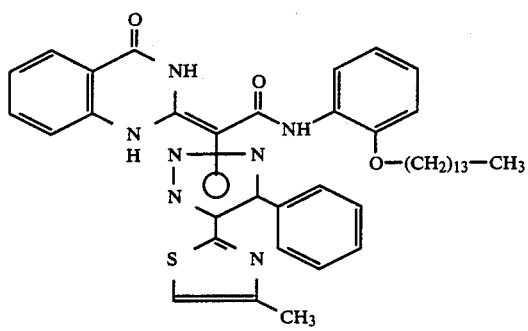
D-10
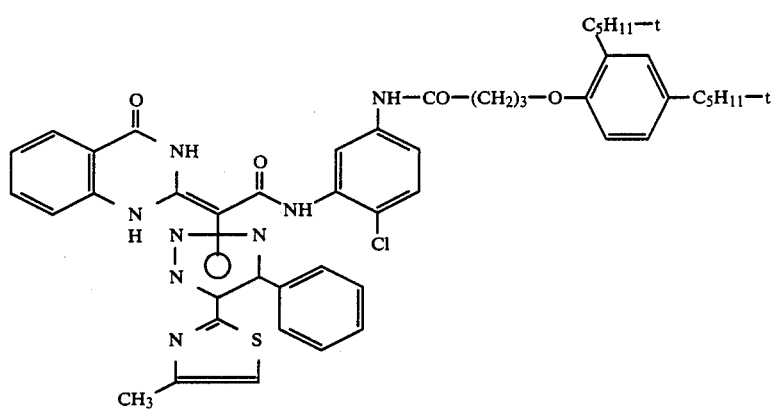
D-11
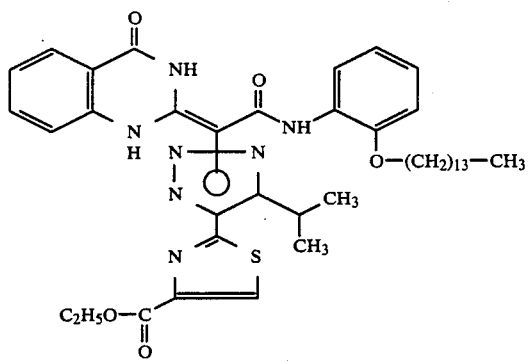
D-12
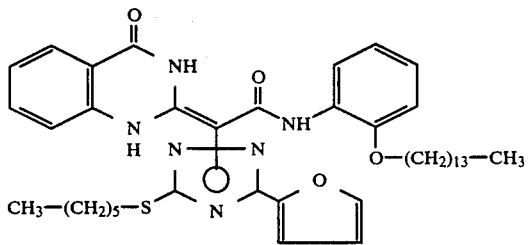

-continued
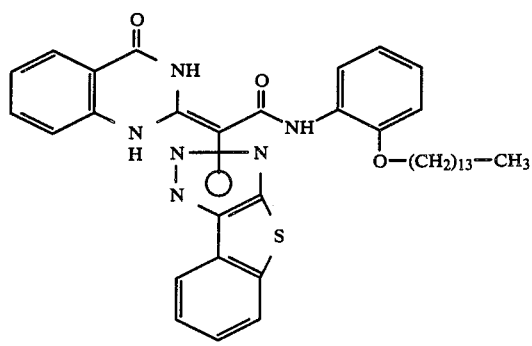
D-13
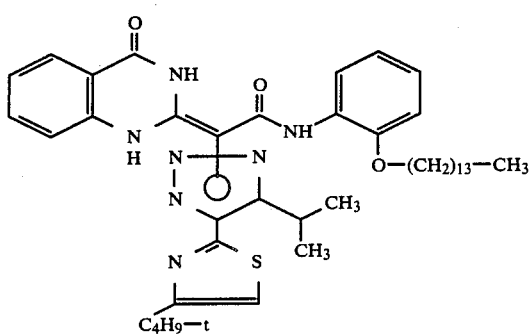
D-14
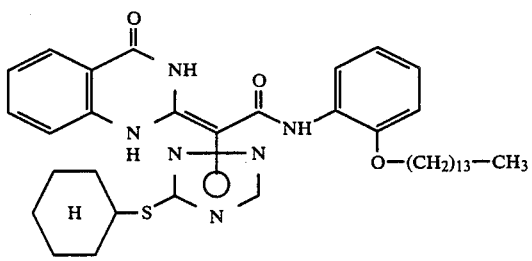
D-15
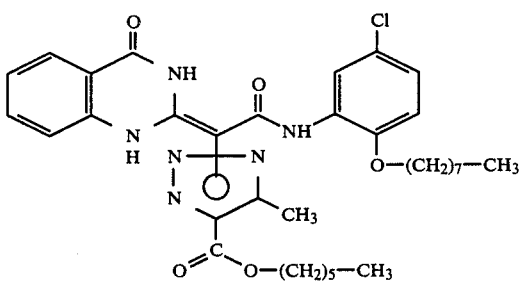
D-16
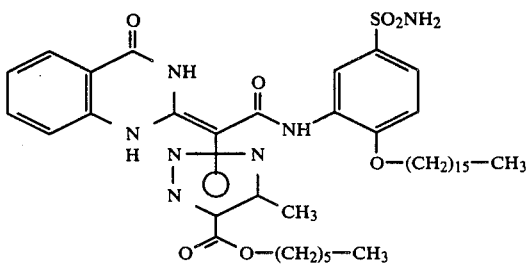
D-17

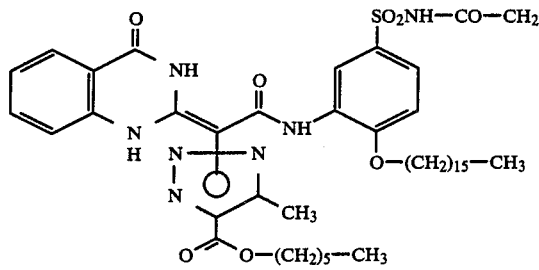
D-18
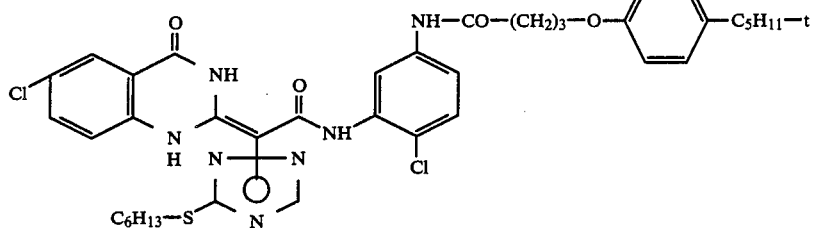
D-19
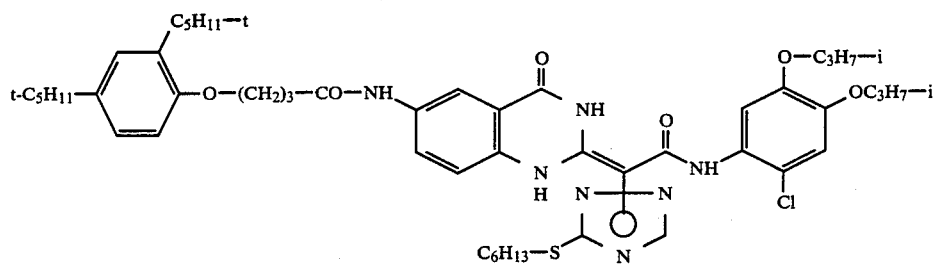
D-20
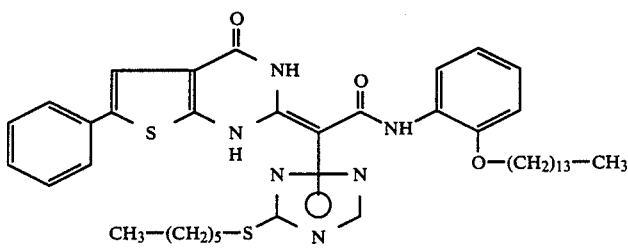
D-21
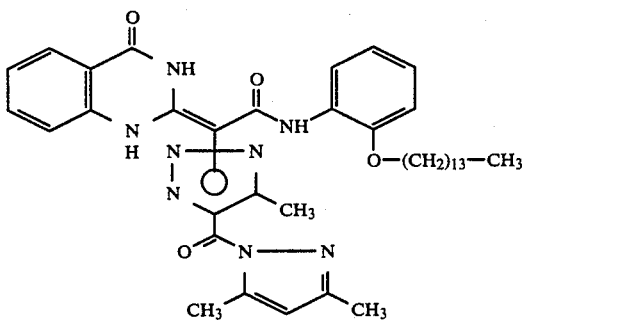
D-22
The couplers according to the invention may be prepared by initially preparing the esters corresponding to general formula III
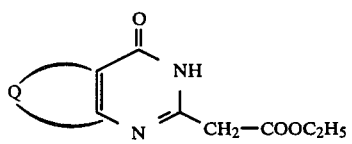
(III)

subsequently converting these esters in known manner into the corresponding 4-equivalent couplers corresponding to general formula IV

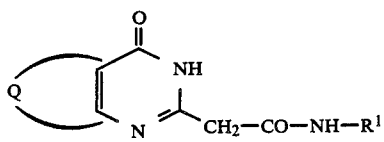 (IV)

from which the couplers according to the invention are obtained by introduction of the group —(TIME)$_n$—X into the coupling position.

The anthranilamides (starting material for the preparation of the quinazolone-2-acetic esters (III) are all prepared by known methods:
(1) ammonolysis of isatoic acid anhydrides
(2) aminolysis of anthranilic acid esters
(3) partial hydrolysis of 2-aminobenzonitriles with acid of alkali
(4) direct ring syntheses.

The following are examples of suitable intermediates:

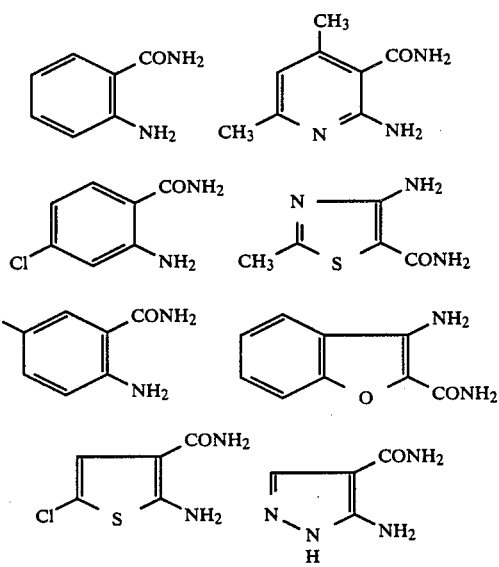

The following are examples of suitable esters of general formula III. Quinazolone-2-acetic esters:

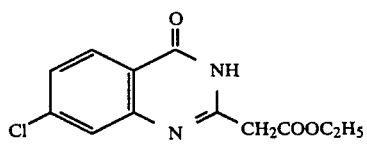

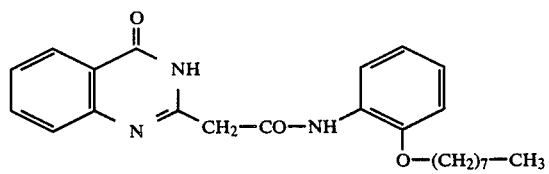

-continued

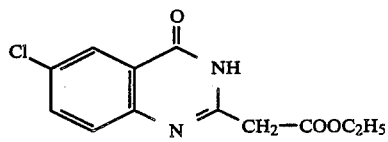

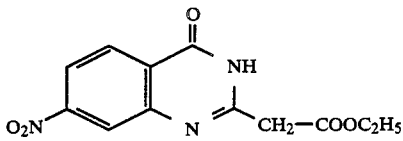

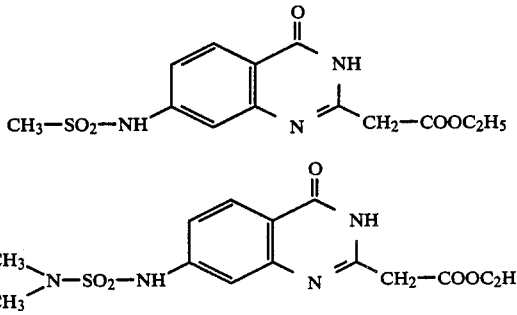

thienopyrimidine-4-one-2-acetic esters, such as:

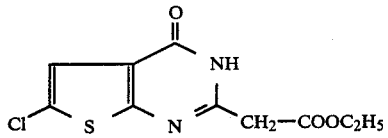

Process for their preparation (for example reaction of malonimino ether ester with 2-aminoaryl carbonamides or reaction of β, β-dialkoxyacrylic acid esters with 2-aminocarbonamides) are described, for example, in GB-A-689 023.

The esters III may also be prepared as follows:
reaction of halogenated quinazolones with acetoacetic ester
extrusion of sulfur from quinazolone-2-ethio-glycolic acid esters using a strong base and/or thiophilic reagents (for example triphenyl-phosphine).

The reaction of the esters III to the amides IV may be carried out either directly by aminolysis, for example at elevated temperature of >120° C., or indirectly via the free acid which may be obtained from the ester by carefully hydrolysis with alkali.

The following are examples of particularly suitable 4-equivalent couplers IV from which the corresponding 2-equivalent couplers according to the invention may be prepared:

IV-1

-continued
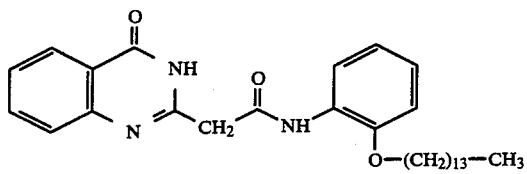
IV-2
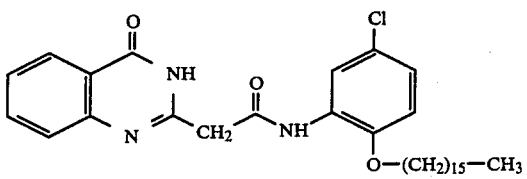
IV-3
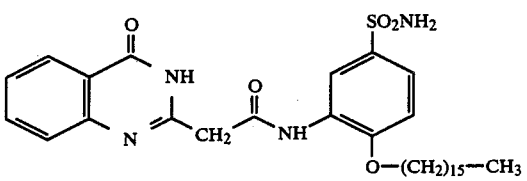
IV-4
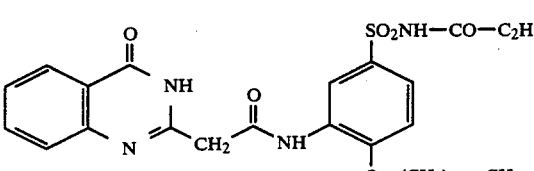
IV-5
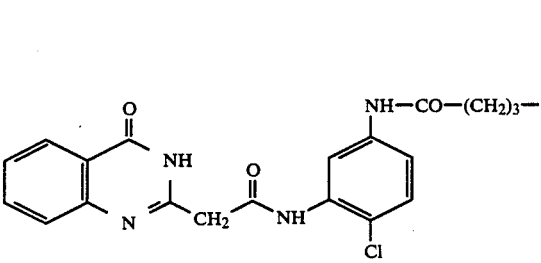
IV-6
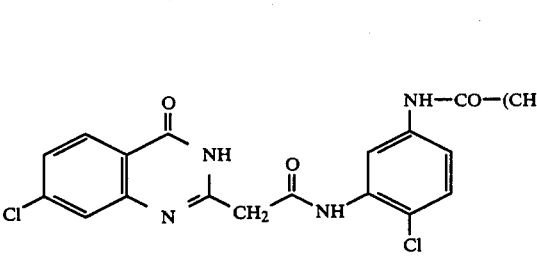
IV-7
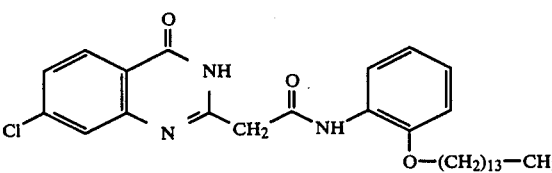
IV-8
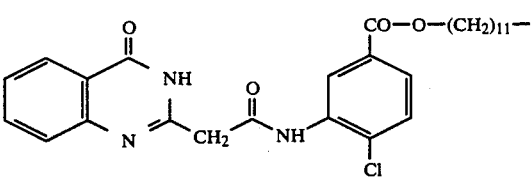
IV-9

-continued

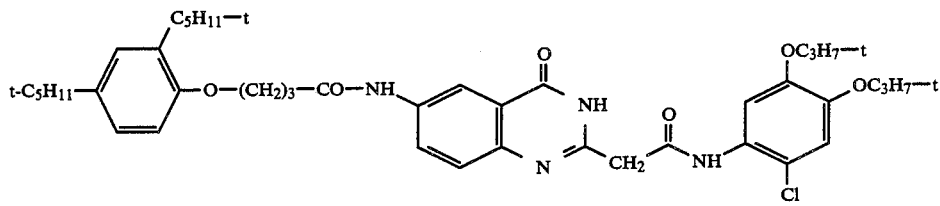
IV-10

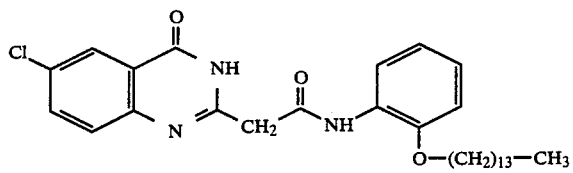
IV-11

The 2-equivalent couplers according to the invention may be obtained form the quinazolone acetamides IV by methods known in the chemistry of 2-equivalent couplers, for example by reaction of the halogenated couplers corresponding to general formula V (for example obtained from the 4-equivalent couplers IV by halogenation with bromine, chlorine or sulfuryl chloride) with a triazole II.

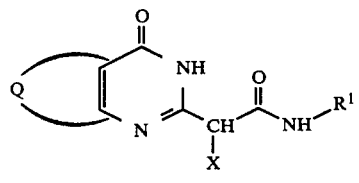

X = Cl, Br (V)

-continued
or

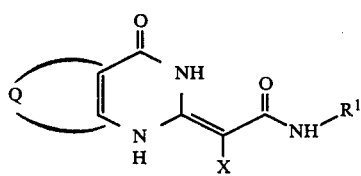
(VI)

According to the results of proton resonance spectra, all the halogenated quinazolone-2-acetamides investigated are present in the keteneaminal form VI, although individual compounds may possibly be present in tautomeric equilibrium with the form V.

The following are particularly suitable halogenated couplers V, for example by virtue of their reactivity, solubility or stability properties:

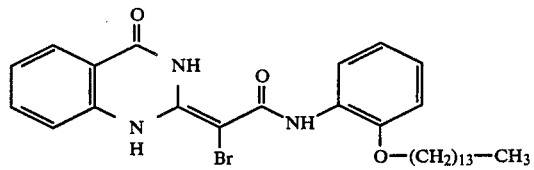
V-2

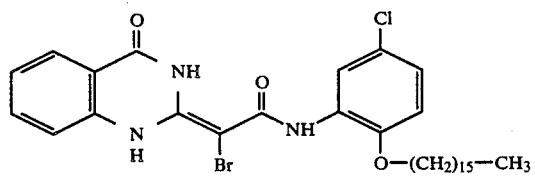
V-3

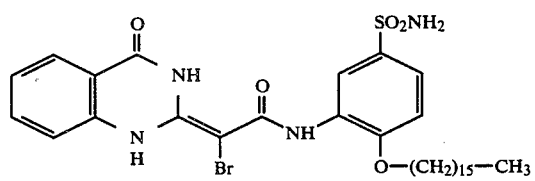
V-4

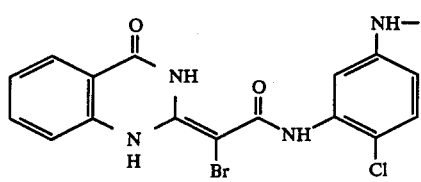

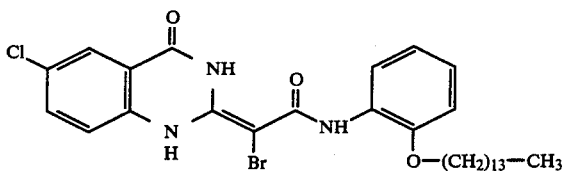

The position at which the triazole ring is attached to the quinazolone methyne residue is not known; on account of the pronounced delocalization of the charge, no particular preference is generally attributed to any one of attachment. In general, isomer mixtures accumulate during the synthesis of the compounds, but do not have to be separated up by virtue of their similar reactivity.

The following are examples of suitable triazoles (preferred releasable groups X according to the invention generally acting as development inhibitors):

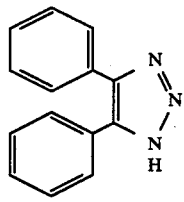

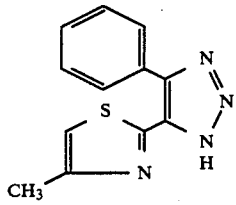

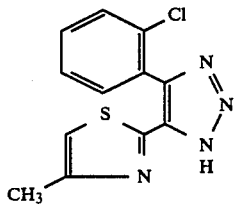

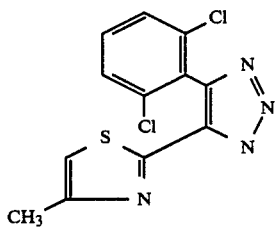

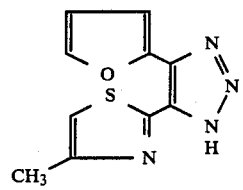

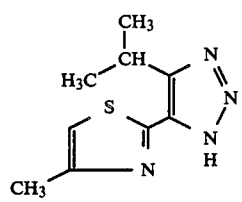

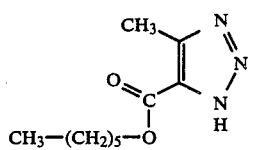

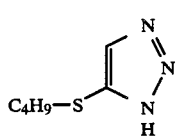

-continued

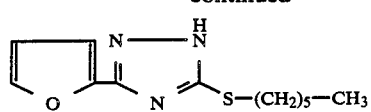
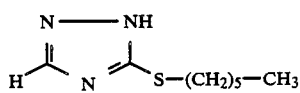
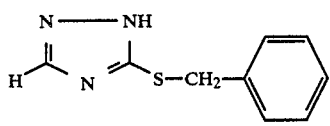
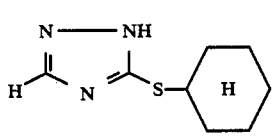
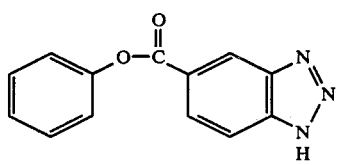
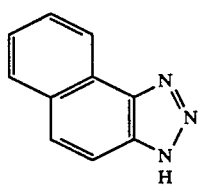
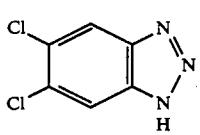
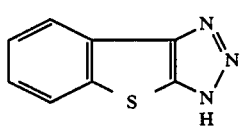
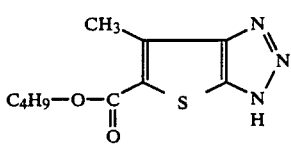
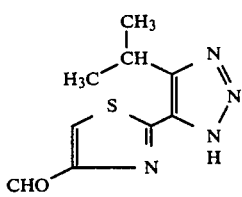

-continued

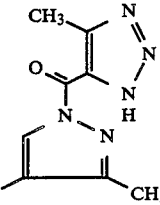
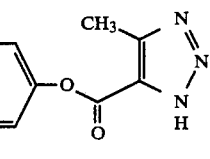
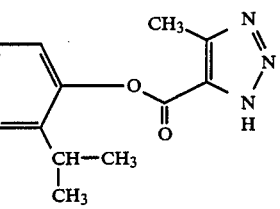
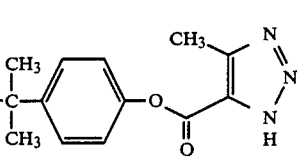
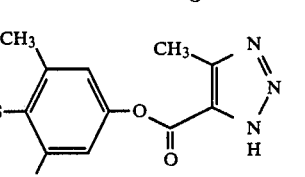

A development-inhibiting, development-accelerating or nucleating effect may also be attributed to triazole compounds which are only converted into the actual effective triazole compound after elimination from the coupler residue by a subsequent hydrolysis step, for example with elimination of an acyl function or cleavage of a lactone ring. Finally, the actual effective development-accelerating or nucleating compound may also be released from the triazole compound released in the coupling step by a hydrolysis step or an elimination step or an intramolecular nucleophilic displacement reaction, in which a possibly only short-lived ring is formed.

An exception are triazoles which contain a residue which is itself capable of coupling or may be converted into a coupling residue by a hydrolysis step.

Accordingly, 2-equivalent couplers according to the invention which release a triazole compound having a development accelerating effect or a nucleating effect act as DAR (development accelerator releasing) couplers. This effect may come about in various ways, for example through the ability of the triazole compound eliminated to form soluble complexes with Aghu = ions, through the consumption of color developer oxidation product at a higher rate than the original coupler, through the formation of a superadditive system in combination with the color developer and, finally, through the reductive formation of developable silver nuclei on previously non-developable silver halide grains in the vicinity of the developing silver halide crystal. Accordingly, the triazole compounds present in the couplers I according to the invention may contain substituents which make the above-mentioned effects possible, for example substituents having a bisthioether structure, a hydrazide structure, a phenylhydrazide structure, a thioether hydrazide structure, a thiourea, dithiocarbamate or thiocyanate structure.

Preparation Examples

Coupler IV-2

A solution of 34.8 g (0.15 mole) 4-keto-3,4-dihydroquinazoline-2-acetic acid ethyl ester (prepared in accordance with Example 1 of GB-A-689 023) and 45.8 g 2-tetradecyloxyaniline in 150 ml p-cymol is heated under reflux for 3 hours with removal of the ethanol released by distillation, stirrred into 400 ml methanol, left overnight to crystallize, filtered under suction and washed with methanol. Crystallization from methyl acetate or acetonitrile gives 49 g white crystals melting at 117°–120° C.

The following 4-equivalent couplers are similarly prepared:

| IV-1 | Mp. | 152–154° C. |
| IV-3 | Mp. | 135–137° C. |
| IV-4 | Mp. | >140° C. with gradual decomposition |
| IV-6 | Mp. | 166–170° C. |
| IV-7 | Mp. | 108–210° C. (from acetic acid) |
| IV-8 | Mp. | 142–143° C. |

All melting points are uncorrected.

Compound V-2 (brominated coupler)

A solution of 9.6 g (0.06 mole) bromine in 50 ml acetic acid is added dropwise with stirring at 25° C. to a suspension of 29.5 g (0.06 mole) coupler IV-2 in 300 ml acetic acid. On completion of bromination, 40 ml water are added. The reaction mixture is left standing overnight, diluted with 400 ml water an filtered under suction. After washing with methanol and drying in air, 27.4 g of a pale cream-colored powder having a decomposition melting point of 130°–132° C. are obtained. The product is purified by recrystallization from methyl ethyl ketone. According to the result of thin-layer chromatography (silica gel, eluent toluene-ethyl acetate 7:3), the purified product does not contain any dibromo compound.

The following compounds for example are prepared by the same method:

| V-3 | Mp. | 135–137° C. |
| V-6 | Mp. | 181–183° C. |

Coupler D-5 (coupler according to the invention)

2.8 g 1,1,3,3-tetramethyl guanidine are added dropwise at room temperature to a suspension of 14.1 g compound V-6 (0.02 mole) and 4.6 g 4-methyl-1,2,3-triazole-5-carboxylic acid n-hexyl ester (0.024 mole) in 50 ml dimethyl acetamide. After 1 hour, the yellow-red solution is poured into 200 ml ice water. The flocculent deposit is filtered under suction, freed from impurities by chromatography with toluene-ethyl acetate on silica gel and recrystallized from acetonitrile. 6.7 g pale yellow crystals melting at 128° C. are obtained.

The following couplers, generally in the form of isomer mixtures, are obtained by the same method:

| Compound: | |
|---|---|
| D-1 | Mp. 115–120° C. |
| D-2 | softens above 170° C., Mp. 195–200° C. |
| D-3 | Mp. 131–133° C. |
| D-4 | 2 isomers after preparative separation isomer A: Mp. 112–114° C. isomer B: Mp. 137–139° C. |

Although the formation of 3 isomers is theoretically possible, only 2 isomers are formed in most cases at temperatures in the range from 10° to 55° C., the formation of a third, occasionally intensively fluorescent isomer only being observed to a significant extent at reaction temperature above 75° C. This isomer is removed during the fractional crystallization of the crude product, generally via the mother liquors.

With most of the 2-equivalent couplers, the individual isomers show comparable coupling activity, although they differ, in some cases considerably, in their solubility. Accordingly, the isomer distribution is not critical and is generally predetermined by steric reasons. However, it also be influenced by the reaction parameters, above all by
1. the polarity of the solvent,
2. the water content of the reaction medium,
3. the choice of the auxiliary base,
4. the reaction temperature.

In general, it is preferred to use an nonprotic medium because the reaction takes place more cleanly and more uniformly, though not necessarily more quickly, therein.

Suitable solvents for the reaction between halogenated and triazole compound are, primarily, dimethyl formamide, dimethyl acetamide, N-methylpyrrolidone, tetramethyl urea, sulfolan, ethyl acetate, butyl acetate, acetonitrile, methyl ethyl ketone, acetone, cyclohexanone, chlorobenzene, toluene, diethyl carbonate.

In general, no more than 1 equivalent is required as auxiliary base. However, excesses are harmless and do not complicate working-up either. Suitable auxiliary bases are organic or inorganic bases, high basicity affording no particular advantages. Particularly favorable auxiliary bases are tetramethyl guanidine, diazabicycloundecane, diazabicyclononane, sodium carbonate, potassium carbonate, potassium tert.-butylate.

The order in which the individual components are added is also not ciritcal, especially since the halogenated couplers generally show poor solubility and only enter into solution during the reaction.

The increase in solubility by which the formation of the triazole-substituted 2-equivalent coupler is generally accompanied and which enables it to be readily incorporated in a photographic recording material is surprising. It may be assumed that this improvement in solubility is associated with the development of intramolecular hydrogen bridge bonds which enable the molecule to form isomers and tautomers in large numbers.

The compounds according to the invention are suitable for example for use as yellow DIR couplers in color photographic, more especially multilayer, recording materials. As yellow couplers, they are preferably used in, or associated with, a photosensitive silver halide emulsion layer predominantly sensitive to the blue spectral region of visible light. The particular advantage of the yellow DIR couplers according to the invention, namely comparatively low inhibition of development in the layer with which such a compound is associated, in addition to comparatively high inhibition of development in adjacent, nonassociated layers, is of course of particular relevance when the multilayer color photographic recording material in question is one which, in addition to a predominantly blue-sensitive silver halide emulsion, contains other photosensitive silver halide emulsion layers predominantly sensitive to the green and red spectral regions of visible light.

By virtue of their high activity, the DIR couplers according to the invention may be used in comparatively small quantities to produce the desired effects, particularly the inter-image effects. This makes it possible, for example, to use the DIR couplers according to the invention not only in the blue-sensitive layers producing yellow dye, but also in other layers without an excessive, undesirable secondary density occurring in those layers. Accordingly, the DIR couplers according to the invention may also be used with advantage in magenta layers and in cyan layers.

In the production of the photosensitive color photographic recording material, the non-diffusing DIR couplers according to the invention may be incorporated in known manner, optionally together with other couplers, in the casting solution of the silver halide emulsion layers or other colloid layers. For example, oil-soluble or hydrophobic couplers may be added to a hydrophilic colloid solution, preferably from a solution in a suitable coupler solvent (oil former), optionally in the presence of a wetting agent or dispersant. The hydrophilic casting solution may of course contain other standard additives in addition to the binder. The solution of the coupler does not have to be directly dispersed in the casting solution for the silver halide emulsion layer or any other water-permeable layer. Instead, it may even be initially dispersed with advantage in an aqueous non-photosensitive solution of a hydrophilic colloid, after which the mixture obtained is mixed with the casting solution for the photo-sensitive silver halide emulsion layer or any other water-permeable layer before application, optionally after removal of the low-boiling organic solvent used.

Suitable photosensitive silver halide emulsions are emulsions of silver chloride, silver bromide or mixtures thereof, optionally with a small content of silver iodide of up to 10 mole %, in any of the hydrophilic binders normally used. Gelatin is preferably used as binder for the photographic layers, although it may also be completely or partly replaced by other natural or synthetic binders.

The emulsions may be chemically and spectrally sensitized in the usual way and the emulsion layers and also any other non-photosensitive layers may be hardened in the usual way with known hardening agents.

Color photographic recording materials normally contain at least one silver halide emulsion layer for recording light of each of the three spectral regions red, green and blue. To this end, the photosensitive layers are spectrally sensitized in known manner by suitable sensitizing dyes. Blue-sensitive silver halide emulsion layers need not necessarily contain a spectral sensitizer because, in many cases, the natural sensitivity of the silver halide is sufficient for recording blue light.

Each of the photosensitive layers mentioned may consist of a single layer or, in known manner, for example as in the so-called double layer arrangement, may also comprise two or even more partial silver halide emulsion layers (DE-C-1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present, they may be arranged immediately adjacent one another or in such a way that a photosensitive layer of different spectral sensitivity is present between them (DE-A-1 958 709, DE-A-25 30 645, DE-A-26 22 922).

Color photographic recording materials for the production of multicolor images normally contain non-diffusing color couplers for producing the different component dye images cyan, magenta and yellow in spatial and spectral association with the silver halide emulsion layers of different spectral sensitivity.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally non-photosensitive binder layer.

By spectral association is meant that the spectral sentivity of each of the photosensitive silver halide emulsion layers and the color of the component dye imagge produced from the particular spatially associated color coupler bear a certain relationship to one another, another color of the component dye image in question (for example cyan, magenta, yellow) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same. They are merely required to produce at least substantially the same color during color development, normally a color complementary to the color of the light to which the silver halide emulsion layers in question are predominantly sensitive.

In preferred embodiments, therefore, at least one non-diffusing color coupler for producing the cyan component dye image, generally a coupler of the phenol or α-naphthol type, is associated with red-sensitive silver halide emulsion layers. Advantageous cyan couplers are described, for example, in EP-A-0 028 099, EP-A-0 067 689, EP-A-0 175 573 and EP-A-0 184 057. At least one non-diffusing color coupler for producing the magenta component dye image, normally a color coupler of the 5-pyrazolone, the indazolone or the pyrazoloazole type, is associated with green-sensitive silver halide emulsion layers. Finally, at least one non-diffusing color coupler for producing the yellow component dye image, generally a color coupler containing an open-chain ketomethylene group, is associated with blue-sensitive silver halide emulsion layers. Color couplers of this type are known in large numbers and are described in a number of patent specifications. Reference is made here, for example, to the publications entitled "Farbkuppler (Color Couplers)" by W. PELZ in "Mitteilungen aus den Forschungslaboratorien der Agfa, Leverkusen/München", Vol. III, page 111 (1961) and by K. VENKATARAMAN in "The Chemistry of Synthetic Dyes", Vol. 4, 341 to 387, Academic Press (1971).

The color couplers may be both typical 4-equivalent couplers and also 2-equivalent couplers in which a smaller quantitiy of silver halide is required for dye production. 2-Equivalent couplers are known to be derived from the 4-equivalent couplers in that they contain in the coupling position a substituent which is eliminated during the coupling reaction. 2-Equivalent couplers include both those which are substantially colorless and also those which have a strong color of their own which either disappears during the color coupling reaction or is replaced by the color of the image dye produced. Couplers of the latter tpye may also be additionally present in the photosensitive silver halide emulsion layers where they serve as masking couplers for compensating the unwanted secondary densities of the image dyes. However, 2-equivalent couplers also include the known white couplers, although couplers such as these do not produce a dye on reaction with color developer oxidation products. 2-Equivalent couplers also include the known DIR couplers, i.e. couplers which, in the coupling position, contain a releasable group which is released as a diffusing development inhibitor on reaction with the developer oxidation products. Other photographically active compounds, for example development accelerators or fogging agents, may also be released from such couplers during development.

According to the invention, the color photographic recording material additionally contains at least one 2-equivalent yellow coupler corresponding to formula I which may be present not only in the yellow layer, but also in the magenta layer and/or even in the cyan layer and also in a non-photosentive layer adjacent one of the layers mentioned.

In addition to the constituents mentioned above, the color photographic recording material according to the invention may contain other additives, such as for example antioxidants, dye stabilizers and agents for influencing the mechanical and electrostatic properties. In order to reduce or avoid the adverse effect of UV light on the dye images produced with the color photographic recording material according to the invention, it is of advantage for example to use UV absorbers in one or more of the layers present in the recording material, preferably in one of the upper layers. Suitable UV absorbers are described, for example, in US-A-3 253 921, in DE-C-20 36 719 and in EP-A-0 057 160.

The usual layer supports may be used for the materials according to the invention, see Research Disclosure no. 17 643, Chapter XVII.

Suitable protective colloids and binders for the layers of the recording material are the usual hydrophilic film-forming agents, for example proteins, more especially gelatin. Casting aids and plasticizers may be used. Reference is made to the compounds mentioned in Research Disclosure no. 17 643, Chapters IX, XI and XII.

The layers of the photographic material may be hardened in the usual way, for example with hardeners of the epoxide type, the heterocyclic ethyleneimine type and the acryloyl type. The layers may also be hardened by the process according to DE-A-22 18 009 to produce color photographic materials which are suitable for high-temperature processing. It is also possible to harden the photographic layers with hardeners of the diazine, triazine or 1,2-dihydroquinoline series or with hardeners of the vinyl sulfone type. Other suitable hardeners are known from DE-A-24 39 551, DE-A-22 25 230, DE-A-23 17 672 and from the above-cited Research Disclosure 17 643, Chapter XI.

Other suitable additives are mentioned in Research Disclosure 17 643 and in "Product Licensing Index" December 1971, pages 107–110.

To produce color photographic images, the color photographic recording material according to the invention is developed with a color developer compound. Suitable color developer compounds are any developer compounds which are capable of reacting with color couplers in the form of their oxidation product to form azomethine dyes. Suitable developer compounds are aromatic compounds containing one primary amino group of the p-phenylenediamine type, for example N, N-dialkyl-p-phenylenediamines, such as N, N-diethyl-p-phenylenediamine, 1-(N-ethyl-N-methylsulfonamidoethyl) -3-methyl-p-phenylenediamine, 1-(N-ethyl-N-hydroxyethyl -3-methyl-p-phenylenediamine, and 1-(N-ethyl-N-methoxyethyl)-3-methyl-p-phenylenediamine.

Other useful color developers are described, for example, in J. Amer. Chem. Soc. 73 3100 (1951) and in G. Haist, Modern Photographic Processing, 1979, John Wiley and Sons, New York, pages 545 et seq.

After color development, the material is bleached and fixed in the usual way. Bleaching and fixing may be carried out separately from or even together with one another. Suitable bleaches are any of the usual compounds, for example $Fe^{3+}$ salts and $Fe^{3+}$ complex salts, such as ferricyanides, dichromates, water-soluble cobalt complexes, etc. Particular preference is attributed to iron (III) complexes of aminopolycarboxylic acids, more especially for example ethylenediamine tetraacetic acid, N-hydroxyethyl ethylenediamine triacetic acid, alkylaminodicarboxylic acids and of corresponding phosphonic acids. Persulfates are also suitable bleaches.

EXAMPLE 1

A color photographic recording material for negative color development was prepared by applying the following layers in the order indicated to a transparent support of cellulose triacetate. The quantities applied are all based on 1 square meter. For the silver halide applied, the corresponding quantities of $AgNO_3$ are indicated. All the silver halide emulsions were stabilized with 0.5 g 4-hydroxy-6-methyl-1,3,3a,7-tetraazaindene per 100 g $AgNO_3$.

Layer 1 (antihalo layer) black colloidal silver sol containing 0.4 g Ag and 3 g gelatin Layer 2 (intermediate layer) 0.5 g gelatin Layer 3 (1st red-sensitized layer) red-sensitized silver bromide iodide emulsion (5 mole % iodide; average grain diameter 0.05 μm) of 3.5 g $AgNO_3$ containing 0.7 g coupler C-1, 0.06 g masking coupler MC-1, DIR coupler as shown in Table 1 and 1.5 g gelatin.

Layer 4 (2nd red-sensitized layer) red-sensitized silver bromide iodide emulsion (10 mole % iodide; average grain diameter 1.5 μm) of 3.7 g AgNO$_3$ containing 0.2 g coupler C-1 and 1.9 g gelatin Layer 5 (intermediate layer) 0.8 g gelatin Layer 6 (1st green-sensitized layer) green-sensitized silver bromide iodide emulsion (5 mole % iodide; average grain diameter 0.5 μm) of 2.5 g AgNO$_3$ containing 0.6 g coupler M-1, 0.07 g masking coupler MC-2, DIR coupler as shown in Table 1 and 1.4 g gelatin Layer 7 (2nd green-sensitized layer) green-sensitized silver bromide iodide emulsion (10 mole % iodide; average grain diameter 1.4 μm) of 2.1 g AgNO$_3$ containing 0.15 g coupler M-1, 0.03 g masking coupler MC-2 and 1.6 g gelatin Layer 8 (yellow filter layer) yellow colloidal silver sol containing 71 mg Ag and 0.5 g gelatin Layer 9 (1st blue-sensitive layer) silver bromide iodide emulsion (5 mole % iodide; average grain diameter 0.7 μm) of 0.5 g AgNO$_3$ containing 0.6 g coupler Y-1, $4.2 \times 10^{-4}$ moles DIR coupler DV-1 and 1.4 g gelatin Layer 10 (2nd blue-sensitive layer) silver bromide iodide emulsion (9 mole % iodide; average grain diameter 1.4 μm) of 1.5 g AgNO$_3$ containing 0.15 g coupler Y-1 and 0.7 g gelatin Layer 11 (protective layer) 0.7 g gelatin Layer 12 (hardening layer) 0.24 g gelatin and 0.7 g carbamoyl pyridinium salt (CAS Reg. no. 65411-60-1)

The following couplers were used:

Coupler C-1

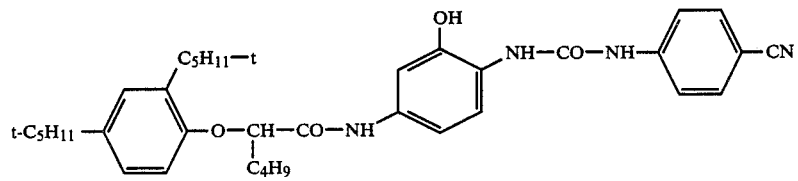

Coupler M-1

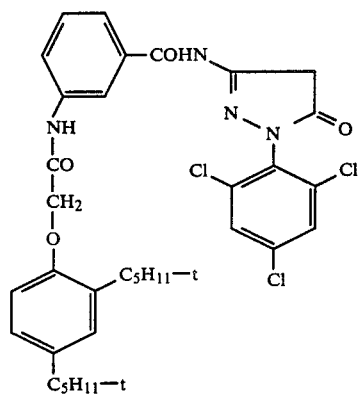

Masking coupler MC-1

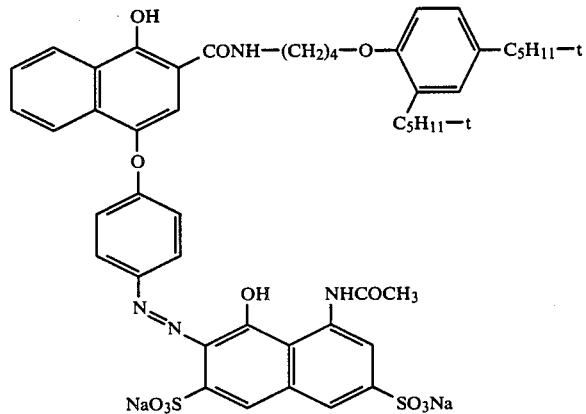

Masking coupler MC-1

-continued

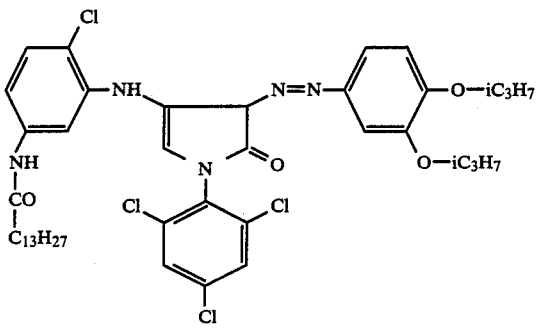

Coupler Y-1

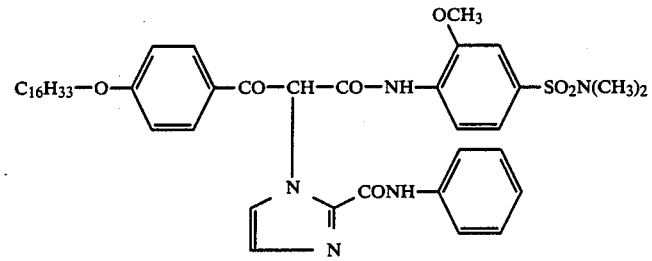

DIR coupler DV-1

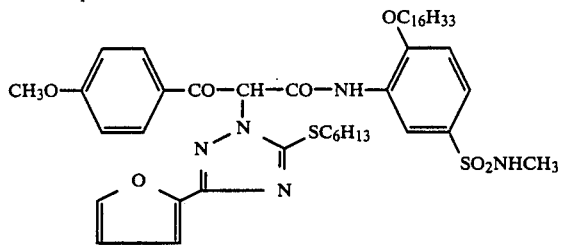

The compounds C-1, MC-2, Y-1 and the DIR couplers were used in the form of dispersions each containing 1 part gelatin, 2 parts tricrsylphosphate in the case of M-1 and M-2 but di-n-butyl phthalate in every other case and 0.1 part of the Na salt of triisopropoyl naphthalenesulfonic acid as wetting agent being used to 1 part of the compound used.

Various versions (materials 1 to 7) of the recording material having the described structure were prepared, differing from one another solely in the DIR couplers used in layers 3 and 6. Development was carried out after exposure behind a grey wedge and color filters, as described in "The Journal of Photography", 1974, pages 597 and 598.

The results obtained after processing are shown in Table 1. The inter-image effects IIE are calculated as follows:

$$IIE_{cy} = \frac{\gamma_{red} - \gamma_w}{\gamma_w} \ ; \ IIE_{mg} = \frac{\gamma_{green} - \gamma_w}{\gamma_w}$$

where
$\gamma_{red}$ = gradation on selective exposure to red light
$\gamma_{green}$ = gradation on selective exposure to green light
$\gamma_w$ = gradation on exposure to white light
$EE_{cy}$ = EE in the red-sensitized layer
$EE_{mg}$ = EE in the green-sensitized layer

TABLE 1

| Material | DIR coupler [× $10^{-5}$ mol] | | $EE_{cy}$ | $EE_{mg}$ | $IIE_{cy}$ | $IIE_{mg}$ |
| | Layer 3 | Layer 6 | | | | |
|---|---|---|---|---|---|---|
| 1 (Comparison) | DV-1 7.1 | DV-1 7.0 | 0.33 | 0.36 | 30 | 28 |
| 2 (Invention) | D-1 4.0 | D-1 4.1 | 0.41 | 0.38 | 41 | 40 |
| 3 (Invention) | D-2 5.1 | D-1 7.0 | 0.38 | 0.41 | 30 | 50 |
| 4 (Invention) | D-3 5.9 | D-3 5.0 | 0.40 | 0.36 | 40 | 35 |
| 5 (Invention) | D-6 5.1 | DV-1 7.0 | 0.38 | 0.36 | 42 | 46 |
| 6 (Invention) | D-7 5.5 | DV-1 7.0 | 0.52 | 0.40 | 50 | 50 |
| 7 (Invention) | D-8 5.1 | DV-1 7.0 | 0.42 | 0.38 | 38 | 40 |

We claim:
1. A color photographic recording material comprising at least one photosensitive silver halide emulsion layer and, associated therewith, a coupler which is capable of releasing a photographically active compound, characterized in that the coupler corresponds to the following general formula

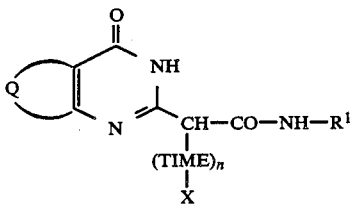

in which
R$^1$ represents alkyl, a heterocyclic or carbocyclic aromatic group or —NH—CO—R$^2$;
R$^2$ represents alkyl, aryl or —NH—R$^3$;
R$^3$ represents alkyl or aryl;
Q represents the residue required to complete a fused, optionally substituted benzene or heterocyclic ring;
X represents the residue of a photographically active compound;
TIME represents a bond which, on reaction of the coupler with the oxidation product of a color developer, is released together with the residue X attached thereto and, in turn, releases the residue X as a photographically active compound under the development conditions; n=0 or 1.

2. A recording material as claimed in claim 1, characterized in that the coupler is a DIR coupler.

3. A recording material as claimed in claims 1 or 2, characterized in that R$^1$ is a phenyl radical substituted by a group which imparts resistance to diffusion in the form of an alkoxy, alkoxycarbonyl, carbamoyl, sulfamoyl, sulfonamido or carbonamido group.

4. A recording material as claimed as claim 1 or 2, characterized in that X represents a group corresponding to the following formula:

in which
Z represents the groups required to complete a 1,2,3- or 1,2,4-triazole ring;
R$^5$ and R$^6$ represent H, alkyl, aryl, a heterocyclic group, alkoxy, —S—R$^7$, amino, acylamino, a carboxylic acid ester group or —CO—NR$^8$NR$^9$, or when the ring completed by Z ia a 1,2,3-triazole ring R$^5$ and R$^6$ together represent the groups required to complete a fused ring;
R$^7$ represents an alkyl, cycloalkyl, aralkyl, alkenyl, alkynyl or aryl;
R$^8$ represents alkyl, aralkyl or aryl;

R$^9$ represnets H or has the same meaning as R$^8$ or R$^8$ and R$^9$ together represent the groups required to complete a cyclic amino group.

5. A recording material as claimed in claim 2, characterized in that the DIR coupler is present in a predominantly blue-sensitive silver halide emulsion layer and in that the recording material contains at least one other predominantly green-sensitive or predominantly red-sensitive silver halide emulsion layer.

6. A recording material as claimed in claim 2, characterized in that the DIR coupler is present in a predominantly red-sensitive silver halide emulsion layer.

7. A color photographic recording material comprising at least one predominantly blue-sensitive silver halide emulsion layer unit with which at least one yellow coupler is associated, a predominantly green-sensitive silver halide emulsion layer unit with which at least one magenta coupler is associated and a predominantly red-sensitive silver halide emulsion layer unit with which at least one cyan coupler is associated, wherein at least one of said predominantly green-sensitive and predominantly red-sensitive silver halide emulsion layer units comprises two or more partial silver halide emulsion layers and at least one said partial layer of the predominantly green-sensitive silver halide emulsion layer unit or of the predominantly red-sensitive silver halide emulsion layer unit contains a DIR coupler corresponding to the following formula:

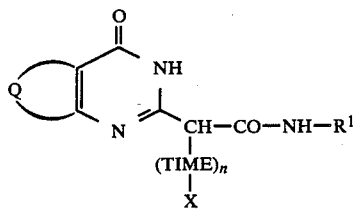

in which
R$^1$ represent alkyl, a heterocyclic or carbocyclic aromatic group or —NH—CO—R$^2$;
R$^2$ represents alkyl, aryl or —NH—R$^3$;
R$^3$ represents alkyl or aryl;
Q represents the groups required to complete a condensed, optionally substituted benzene or heterocyclic ring;
X represents the residue of a development inhibitor;
TIME is a bond which, on reaction of the coupler with the oxidation product of a color developer, is released together with the residue X attached thereto and, in turn, releases the residue X as a development inhibitor under the development conditions;
n=0 or 1.

* * * * *

UNITED STATES PATENT AND TRADEMARK OFFICE
CERTIFICATE OF CORRECTION

PATENT NO. : 4,870,000

DATED : September 26, 1989

INVENTOR(S) : Peter Bergthaller, et al.

It is certified that error appears in the above-identified patent and that said Letters Patent is hereby corrected as shown below:

TITLE PAGE:
In the Abstract, at line 7, "compounds" should read
-- compound -- .

Column 1, line 13, "present" should read -- presence -- .

Column 1, line 19, "call" should read -- called -- .

Column 1, line 66, "neccessary" should read -- necessary -- .

Column 3, line 13, "tming" should read -- timing -- .

Column 3, lines 35-37, please delete the stray mark above the X in the formula:

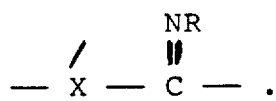

UNITED STATES PATENT AND TRADEMARK OFFICE
CERTIFICATE OF CORRECTION

PATENT NO. : 4,870,000
DATED : September 26, 1989
INVENTOR(S) : Peter Bergthaller, et al.

It is certified that error appears in the above-identified patent and that said Letters Patent is hereby corrected as shown below:

Column 13, formula D-19, the left-hand portion of the formula D-19 should read:

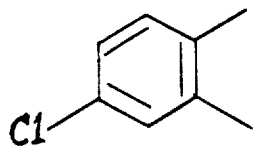

Column 19, line 12, "form the" should read -- from the --.

Column 24, line 63, "Aghu =" should read -- Ag + --.

Column 25, line 19, "stirrred" should read -- stirred --.

Column 25, line 43, "an" should read -- and --.

Column 26, line 53, "ciritcal" should read -- critical --.

Column 29, line 26, "tpye" should read -- type --.

UNITED STATES PATENT AND TRADEMARK OFFICE
CERTIFICATE OF CORRECTION

PATENT NO. : 4,870,000
DATED : September 26, 1989
INVENTOR(S) : Peter Bergthaller, et al.

It is certified that error appears in the above-identified patent and that said Letters Patent is hereby corrected as shown below:

Column 30, line 66, "0.05 µm" should read -- 0.5 µm -- .

Column 35, line 50, In Claim 4, "ia" should read -- is -- .

Column 36, line 1, In Claim 4, "represnets" should read -- represents -- .

Signed and Sealed this

Seventh Day of May, 1991

Attest:

HARRY F. MANBECK, JR.

Attesting Officer

Commissioner of Patents and Trademarks